United States Patent [19]

Arashi et al.

[11] 3,959,343
[45] May 25, 1976

[54] PROCESS FOR PRODUCING HYDRAZONITRILES

[75] Inventors: Masanori Arashi, Tokyo; Hisahiko Shimada, Ashiya; Shigeyuki Fujituka, Tokorozawa; Kimio Kamiya, Kawagoe; Tomoyuki Miyazaki, Fujisawa, all of Japan

[73] Assignee: Wako Pure Chemical Industries, Ltd., Osaka, Japan

[22] Filed: Oct. 25, 1974

[21] Appl. No.: 518,202

[52] U.S. Cl. .................... 260/465.5 R; 260/192; 260/464; 260/465 D; 260/465 E; 260/465.4
[51] Int. Cl.² ........................................ C07C 120/00
[58] Field of Search .......... 260/465.5 R, 464, 465.4, 260/192, 465.5 D

[56] References Cited
UNITED STATES PATENTS

| | | | |
|---|---|---|---|
| 2,469,358 | 5/1949 | Alderson, Jr. et al. | 260/465.5 R |
| 2,565,573 | 8/1951 | Pease et al. | 260/192 |
| 3,192,196 | 6/1965 | Vidal et al. | 260/192 |
| 3,346,554 | 10/1967 | Fuchs | 260/465.5 R X |
| 3,382,281 | 5/1968 | Jankowski et al. | 260/465.5 R X |
| 3,390,146 | 6/1968 | Nield et al. | 260/465.5 R X |
| 3,775,395 | 11/1973 | Koyanagi et al. | 260/465.5 R X |
| 3,876,622 | 4/1975 | Motokawa et al. | 260/192 X |

FOREIGN PATENTS OR APPLICATIONS

| | | | |
|---|---|---|---|
| 1,206,432 | 12/1965 | Germany | 260/192 |

*Primary Examiner*—Joseph P. Brust
*Attorney, Agent, or Firm*—Armstrong, Nikaido & Wegner

[57] ABSTRACT

A ketazine is reacted with hydrogen cyanide in the presence of at least one salt of a metal selected from the group consisting of zinc, tin, iron, copper, aluminum, antimony, tellurium and bismuth, whereby a hydrazo compound is formed. This hydrazo compound is oxidized with a halogen or the like to obtain an azonitrile. The thus obtained azonitrile is useful as a radical polymerization initiator, photo-polymerization initiator, blowing agent or the like.

8 Claims, No Drawings

PROCESS FOR PRODUCING HYDRAZONITRILES

This invention relates to a process for producing azonitriles which are useful as radical polymerization initiators, photo-polymerization initiators, blowing agents, etc., and to a process for preparing intermediates for the azonitriles. More particularly, the invention is concerned with an improved process for preparing a hydrazo compound by reacting a ketazine with hydrogen cyanide in the presence of at least one salt of a metal selected from the group consisting of zinc, tin, iron, copper, aluminum, antimony, tellurium and bismuth, and to a process for producing an azonitrile by use of said hydrazo compound.

As typical azonitriles available at present, there may be shown 2,2′-azobisisobutyronitrile, 2,2′-azobis(2,4-dimethyl-valeronitrile), 1,1′-azobis(cyclohexane-1-carbonitrile) and 2,2′-azobis(2,4-dimethyl-4-methoxy-valeronitrile). These azonitriles have such advantages that they are not only stable to peroxides and to impact and high in safety during application, transportation and storage, but also decompose at one stage without self-induction decomposition, so that polymerization reactions using them can be easily controlled to make it possible to obtain polymers excellent in physical properties. Recently, therefore, the azonitriles have come to be evaluated with increasing interest and have extensively been used as polymerization initiators for, for example, vinyl chloride, acrylonitrile and methyl methacrylate.

Further, a series of azonitriles have also been studied as radical polymerization initiators and photo-polymerization initiators, and many azonitriles having various polymerization activities have been reported.

For the production of these azonitriles, a variety of processes have been proposed, and the industrial scale production thereof is ordinarily carried out by preparing a ketazine from a corresponding ketone and hydrazine, reacting the ketazine with hydrogen cyanide to form a hydrazo compound, and then oxidizing the hydrazo compound with a halogen to obtain a desired azonitrile. However, the known processes have various drawbacks in that although it is necessary from the ordinary chemical knowledge to use the hydrogen cyanide in large excess and to elevate the reaction temperature and pressure so as to accelerate the reaction rate and increase the reaction yield, the elevation of reaction temperature is naturally limited since the hydrazo compound is unstable at elevated temperatures, the elevation of reaction pressure is limited from the safety of reaction operation, and the use of hydrogen cyanide in large excess is restricted from the economical standpoint and the safety of reaction operation. Accordingly, the development of a process for producing azonitriles safely, easily and economically has incessantly been demanded in vain, and it is the actual state that for the production of azonitriles, the hydrogen cyanide is used in large excess and the reaction is conducted for a long period of time.

With an aim to overcome the above-mentioned drawbacks, the present inventors made extensive studies to accomplish the present invention.

An object of the present invention is to provide a process for producing azonitriles safely and economically and in high yields, overcoming the drawbacks of the conventional processes.

Another object of the invention is to provide a process for preparing, in high yields and safely, hydrazo compounds which are intermediates for production of azonitriles.

Other objects and advantages of the invention will become apparent from the explanation given below.

In accordance with the present invention, there is provided a process for producing an azonitrile of the formula,

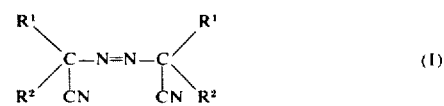

wherein $R^1$ is $C_1 - C_6$ alkyl, phenyl, benzyl, substituted benzyl, $C_3 - C_6$ cycloalkyl, $(C_1 - C_4$ alkoxy$)C_1 - C_4$ alkyl or $(C_1 - C_3$ alkyl)-carboxyl radical; and $R^2$ is $C_1 - C_4$ alkyl, and further $R^1$ together with $R^2$ may form cycloalkyl, which comprises reacting a ketazine of the formula,

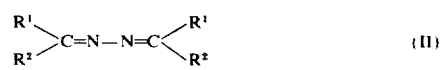

wherein $R^1$ and $R^2$ are as defined above, with hydrogen cyanide in the presence of at least one salt of a metal selected from the group consisting of zinc, tin, iron, copper, aluminum, antimony, tellurium and bismuth, to yield a hydrazo compound of the formula,

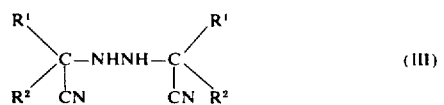

wherein $R^1$ and $R^2$ are as defined above, and then oxidizing the hydrazo compound of the formula (III).

The $C_1 - C_6$ alkyl is straight chain or branched-chain alkyl and includes, for example, methyl, ethyl, n-propyl, isopropyl, n-butyl, isobutyl, tertbutyl, n-amyl, isoamyl, 2-methylbutyl, 2,2-dimethylpropyl. The $C_3 - C_6$ -cycloalkyl includes, for example, cyclopropyl, cyclobutyl, cyclopentyl, cyclohexyl. The $C_1 - C_4$ alkoxy includes, for example, methoxy, ethoxy, n-butoxy.

In the present invention, an excellent improvement, which is not seen in the conventional processes, exists in the preparation of hydrazo compound of the formula (III).

The hydrazo compound of the formula (III) can be prepared in high yield by reacting a ketazine of the formula (II) with hydrogen cyanide in the presence of at least one salt of a metal selected from the group consisting of zinc, tin, iron, copper, aluminum, antimony, tellurium and bismuth.

The salt of a metal selected from the group consisting of zinc, tin, iron, copper, aluminum, antimony, tellurium and bismuth includes, for example, sulfates, chlorides, bromides, bromates, acetates, nitrates, oxalates and succinates of said metals. Among these, particularly effective salts are stannous chloride, zinc acetate, and halides such as chlorides and bromides of zinc, tin, iron, copper, aluminum, antimony, tellurium and bismuth which are Friedel-Crafts catalysts. Among these, zinc chloride, anhydrous aluminum chloride and anhydrous ferric chloride are more preferable.

The ketazine of the formula (II), which is used as starting material, includes, for example, dimethylketazine, methylethylketazine, methylpropylketazine, methylisopropylketazine, methylcyclopropylketazine, methylisobutylketazine, methyl-2-methoxyisobutylketazine, methylcyclohexylketazine, methylphenylketazine, methylisoamylketazine, methylcycloheptylketazine, methylneopentylketazine, diethylketazine, diisopropylketazine, di-n-butylketazine, diisobutylketazine, cyclohexanoneazine, cycloheptanoneazine, methyl-2-carboxyethylketazine, methylbenzylketazine, methyl-4-chlorobenzylketazine and methyl-4-nitrobenzylketazine.

The reaction temperature, the reaction time and the amount of catalyst used, of course, vary depending on the kinds of catalyst and reaction product. Ordinarily, however, the reaction is carried out at 10° to 40°C for 1 to 10 hours in the presence of, preferably, 0.1 to 10% by weight of a catalyst. The reaction is preferably effected in an anhydrous state.

The thus obtained hydrazo compound of the formula (III) is oxidized with, for example, a halogen to give an azonitrile of the formula (I). The oxidation reaction is carried out at −20° to 40°C, preferably below 30°C. The reaction solvent used in this case is one or more of water and organic solvents such as, for example, methanol, ethanol, diethyl ether, chloroform, carbon tetrachloride which are inert to the starting material and the product. After completion of the reaction, the resulting azonitrile is preferably crystallized by adding water in case the solvent is water-soluble or by removing the solvent by distillation in case it is water-insoluble.

The present invention has made it possible to obtain hydrazo and azo compounds in high yields in short periods of time using a substantially theoretical amount of hydrogen cyanide. Thus, the present invention greatly contributes to the art of this field.

What is worthy of special mention is that 2,2'-azobis(2,4-dimethyl-valeronitrile), which is an azonitrile obtained according to the present invention, is markedly high in content of low melting isomer. As is clear from the report of C. G. Overberger in Journal of American Chemical Society, Vol. 73, page 2618, an azo compound is a mixture of isomers, which vary in their configurations or so-called distortions, and in the case of 2,2'-azobis(2,4-dimethyl-valeronitrile), the decomposition rate constant K (sec$^{-1}$ × 10$^4$) of low melting compound (m.p. 56° to 57°C) is 2.89 (69.9°C) while that of high melting compound (m.p. 74° to 76°C) is 1.98 (69.8°C), and thus the low melting compound is higher in decomposition rate constant. Thus, the present invention is of importance in that it provides a novel polymerization initiator which is higher in activity than the conventional mixture.

The present invention is illustrated in more detail below with reference to examples.

Example 1

Into a mixture comprising 196 g of methylisobutylketazine and 2 g of zinc chloride was added dropwise 56 g of anhydrous hydrogen cyanide with stirring and water-cooling at 20° to 35°C. The resulting mixture was reacted at said temperature for 5 hours to deposit crystals. The crystals were recovered by filtration and washed with water to obtain 248 g of 2,2'-hydrazobis(2,4-dimethyl-valeronitrile). To this compound was added 400 ml of methanol, and 75 g of chlorine was introduced at below 25°C into the resulting mixture. Thereafter, 400 ml of water was added, and the mixture was cooled to deposit crystals. The crystals were recovered by filtration and then dried to obtain 246 g of 2,2'-azobis(2,4-dimethylvaleronitrile), m.p. 52° − 56°C. According to infrared absorption spectrum analysis, it was identified that the product was composed substantially of a low melting compound.

The above-mentioned reaction was repeated, except that the zinc chloride was replaced by any of the metal salts shown in Table 1. The amount of the product obtained was as set forth in Table 1, in which is also shown the amount of the product obtained by using no metal salt of the present invention.

Table 1

| Metal salt | Amount of product obtained (g) |
|---|---|
| None | 186 (75%) |
| Anhydrous aluminum chloride | 243 |
| Anhydrous aluminum bromide | 238 |
| Anhydrous ferric chloride | 240 |
| Anhydrous tin tetrachloride | 228 |
| Stannous chloride, dihydrate | 215 |
| Anhydrous zinc acetate | 213 |
| Anhydrous telluric chloride | 217 |
| Anhydrous bismuth chloride | 218 |
| Anhydrous antimony pentachloride | 215 |
| Anhydrous titanium tetrachloride | 218 |
| Zinc sulfate, dihydrate | 210 |
| Ferrous oxalate | 213 |
| Zinc nitrate | 218 |
| Anhydrous tellurous chloride | 220 |
| Anhydrous zinc bromide | 241 |

Example 2

Into a mixture comprising 500 ml. of methanol, 1 mole of the ketazine shown in Table 2 and 2 g of zinc chloride was added dropwise 56 g of anhydrous hydrogen cyanide with stirring at 20° to 25°C. The resulting mixture was reacted at said temperature for 5 hours. After washing, into the reaction mixture was added dropwise at 20° to 30°C 170 g of bromine in 400 ml methanol. Thereafter, the mixture was charged with 400 ml of water and then cooled to deposit crystals, which were then recovered by filtration to obtain the desired azonitrile. The amount of the product obtained was as set forth in Table 2.

Table 2

| Starting material | Amount of product obtained (g) | Yield (%) |
|---|---|---|
| Methylisobutylketazine | 245 | 99 |
| Methyl-2-methoxyisobutyl-ketazine | 218 | 71 |
| Methylisoamylketazine | 262 | 95 |
| Diisopropylketazine | 264 | 95.5 |
| Cyclohexanoneazine | 239 | 98 |
| Methylbenzylketazine | 300 | 95 |
| Methyl-2-carboxyethyl-ketazine | 241 | 86 |

Example 3

Into a mixture comprising 196 g of methylisobutylketazine and 6 g of zinc chloride was added dropwise 675 g of a 12% aqueous hydrogen cyanide solution with stirring at 20° to 35°C. The resulting mixture was reacted at said temperature for 10 hours to deposit crystals. The crystals were recovered by filtration and washed with water to obtain 213 g (yield 85%) of 2,2′-hydrazobis(2,4-dimethyl-valeronitrile). To this compound was added 400 ml of methanol, and 70 g of chlorine was introduced at below 25°C. into the resulting mixture. Thereafter, 400 ml of water was added, and the mixture was cooled to deposit crystals. The crystals were recovered by filtration and then dried to obtain 210 g of 2,2′-azobis(2,4-dimethyl-valeronitrile), m.p. 48°– 63°C.

What is claimed is:

1. A process for preparing a hydrazo compound of the formula,

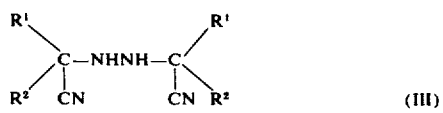
(III)

wherein $R^1$ is $C_1 - C_6$ alkyl, phenyl, benzyl, benzyl substituted with nitro or chloro, $C_3 - C_6$ cycloalkyl, ($C_1 - C_4$ alkoxy)-$C_1 - C_4$ alkyl or ($C_1 - C_3$ alkyl)-carboxyl radical; and $R^2$ is $C_1 - C_6$ alkyl, or $R^1$ together with $R^2$ may form cycloalkyl, which process comprises reacting a ketazine of the formula,

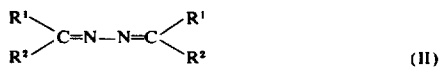
(II)

wherein $R^1$ and $R^2$ are as defined above, with hydrogen cyanide at a temperature of from 10°C to 40°C and 0.1 to 10% by weight, based on the weight of the ketazine, of a sulfate, chloride, bromide, bromate, acetate, nitrate, oxalate or succinate of a metal selected from the group sonsisting of zinc, tin, iron, copper, aluminum, antimony, tellurium and bismuth.

2. A process according to claim 1, wherein the ketazine of the formula (II) is one member selected from the group consisting of dimethylketazine, methylethylketazine, methylpropylketazine, methylisopropylketazine, methylcyclopropylketazine, methylisobutylketazine, methyl-2-methoxyisobutylketazine, methylcyclohexylketazine, methylphenylketazine, methylisoamylketazine, methylcycloheptylketazine, methylneopentylketazine, diethylketazine, diisopropylketazine, di-n-butylketazine, diisobutylketazine, cyclohexanoneazine, cycloheptanoneazine, methyl-2-carboxyethylketazine, methylbenzylketazine, methyl-4-chlorobenzylketazine and methyl-4-nitrobenzylketazine.

3. A process according to claim 1, wherein the ketazine of the formula (II) is methylisobutylketazine.

4. A process according to claim 1, wherein the salt of a metal is stannous chloride, zinc acetate or a Friedel-Crafts catalyst.

5. A process according to claim 1, wherein the salt of a metal is zinc chloride, anhydrous aluminum chloride or anhydrous ferric chloride.

6. A process according to claim 1, wherein the reaction is effected in an anhydrous state.

7. A process according to claim 1, wherein 2,2′-hydrazobis(2,4-dimethyl-valeronitrile) is prepared by reacting methylisobutylketazine with hydrogen cyanide in the presence of zinc chloride at 20° to 35°C.

8. A process according to claim 1, wherein $R^1$ is benzyl substituted with mono-nitro or mono-chloro.

* * * * *